(12) United States Patent
Paufique

(10) Patent No.: US 6,214,361 B1
(45) Date of Patent: Apr. 10, 2001

(54) PROCESS FOR THE EXTRACTION OF AN ACTIVE PRINCIPLE FROM TOURNESOL, ACTIVE PRINCIPLE OBTAINED, AND COMPOSITION ACTIVE AGAINST AGING OF THE SKIN

(75) Inventor: Jean-Jacques Paufique, Objat (FR)

(73) Assignee: S.A. Societe Industrielle Limousine d'Application Biologique (SILAB), Objat (FR)

( * ) Notice: Subject to any disclaimer, the term of this patent is extended or adjusted under 35 U.S.C. 154(b) by 0 days.

(21) Appl. No.: 09/482,886

(22) Filed: Jan. 14, 2000

(30) Foreign Application Priority Data

Dec. 16, 1999 (FR) .................................................. 99 16099

(51) Int. Cl.$^7$ ............................. A01N 65/00; A61K 6/00
(52) U.S. Cl. ...................... 424/401; 424/195.1; 424/401; 514/844; 514/847
(58) Field of Search ............................... 424/195.1, 401; 514/844, 847

(56) References Cited

U.S. PATENT DOCUMENTS 4,215,040 * 7/1980 Hager ................................. 260/123.5
5,683,710 * 11/1997 Akemi et al. ........................ 424/448

FOREIGN PATENT DOCUMENTS 271 261    8/1989  (DE) .
2 657 256  7/1991  (FR) .
2 779 346  12/1999 (FR) .

OTHER PUBLICATIONS

XP–002147747, "Characterization of enzymatic sunflower protein hydrolysates", *Journal of Agricultural and Food Chemistry,* AN 94(03):G0026 (1994).
XP–002147748, "Production of protein isolates from extracted sunflower grits", *Acta Alimentaria,* AN 85(03):G0017 (1985).
XP–002147749, "Optimization of the enzymic treatment during aqueous oil extraction from sunflower seeds", *Food Chemistry,* AN 1998:287902 (1998).
XP–002147750, "Removal of chlorogenic acid from sunflower seeds and meals", AN 79(09):G0786 (1979).

* cited by examiner

*Primary Examiner*—Thurman K. Page
*Assistant Examiner*—S. Tran
(74) *Attorney, Agent, or Firm*—Young & Thompson

(57) ABSTRACT

The object of the invention covers an extraction process for an active principle having anti-radical and anti-glycolation action to counter cutaneous aging. The invention also covers the obtained active principle, the cosmetic compositions using this active principle, and a process for countering aging.

18 Claims, 2 Drawing Sheets

| Product | Concentration | % inhibition of glycolation |
|---|---|---|
| Reference | – | 0% |
| chlorogenic Acid (0,7 g/l) | 5% | 20% |
| active Principle | 3%<br>5%<br>7% | 31%<br>42%<br>54% |

| Product | Concentration | % inhibition of glycolation |
|---|---|---|
| Reference | – | 0% |
| chlorogenic Acid (0,7 g/l) | 5% | 20% |
| active Principle | 3% 5% 7% | 31% 42% 54% |

PROCESS FOR THE EXTRACTION OF AN ACTIVE PRINCIPLE FROM TOURNESOL, ACTIVE PRINCIPLE OBTAINED, AND COMPOSITION ACTIVE AGAINST AGING OF THE SKIN

The present invention relates to a process for the extraction of an active principle of vegetable origin, in this instance from de-oiled tournesol or sunflower seeds, to counter cutaneous aging.

The invention also covers the active principle obtained and the corresponding compositions.

It is known that the reaction of protein glycolation also called the Maillard reaction, is involved in the process of molecular and tissue aging.

This glycolation reaction is in fact a group of successive reactions. In the absence of suitable enzymes, a reaction takes place between a primary free amine function and a reducing function of a reducing sugar such as glucose, to produce glycolated protein. The latter can then undergo a glyco-oxidation reaction. These reactions lead to very stable end compounds rich in double bonds which when broken give irreversible cross-linkages.

One can counter accelerated aging, particularly of the skin, by limiting or retarding this glycolation phenomenon because the glycolic proteins thus cross-linked lose their biological functionality, the tissues rigidify and harden.

Moreover, there exists another well-known factor which also contributes to cutaneous aging, namely free radicals.

Thus, the glycolated proteins react with oxygen and form free radicals such as super oxides. These compounds can initiate the degradation of certain proteins and/or alter the membrane structures. Similarly, the accumulation of free radicals in tissue also catalyzes the glycolation reaction of the proteins which lose their biological properties.

The glycolation reaction can also modify the properties of the macromolecules that are constituents of the extra-cellular matrix, such as the proteoglycanes, the glycoproteins, elastins and collagens.

The formation of irreversible cross-linkages renders the fibrous collagen molecules for example more fragile and the terminal compounds of the glycolation reaction also modify the synthesis of the macroproteins of the extra-cellular matrix. These compounds modify the metabolism of the fibroblasts.

The glycolic proteins also become resistant to the action of proteases, the collagen resists the action of collagenase and the renewal of the collagen is not ensured, which leads to broken and altered tissues.

The active principle according to the invention has for its object to counter the undesirable glycolation actions by two actions:

a powerful anti-oxidant and anti-radical action, by the presence of phenolic acids which trap the free radicals and limit the oxidation reactions, and occupation by glycopeptides of the protein sites involved in specific glucose/protein bonds, preventing the bridges so as to abort the glycolation reaction.

The present invention covers a process for the extraction of an active principle from de-oiled sunflower seeds as well as the active principle obtained. The invention also covers the obtained compositions.

The various accompanying drawings show the results obtained during different tests of the characterization of the active principle extracted and its activity.

The process for extraction according to the present invention will now be described in detail, followed by the characterization of the active principle and the tests of cosmetic effectiveness.

I/ Extraction Process

The extraction process of the active principle according to the present invention consists in the series of the following steps:

crushing sunflower seeds to obtain on the one hand an oil, and on the other hand a de-oiled flour, aqueous solubilization of this obtained flour, in the amount of 10 to 40% by volume, hydrolysis of the proteins in the presence of a protease of acid pH, separation of the soluble and insoluble phases, by decantation, by centrifugation or by filtration, inactivation of this hydrolyzed solution with a pH comprised between 2.0 and 8.0, and a temperature at least equal to 45° C., filtration to purify the active molecules, and sterilizing filtration on a membrane so as to limit the presence of microorganisms, of total mesophilic flora, of yeasts, of molds.

II/ Characterization of the Active Principle

The active principle from this process is characterized by the following composition and by the following characteristics:

1/ Dry Material

The quantity of dry material is greater than 10 g/l, particularly comprised between 10 and 100 g/l and more particularly between 25 and 38 g/l. This range is determined by passage through an oven at 105° C. until a constant weight is obtained.

2/ pH

The value of pH is comprised between 3.0 and 10.0, more particularly between 5.0 and 6.0, obtained by the potentiometric method.

3/ Protein Content

The content is comprised between 5 and 30 g/l, more particularly between 6 and 10 g/l.

Total nitrogen is determined by the KJELDAHL method (official method of analysis of the A.O.C. 1975, 12th ed W. Horwitz, NY, p. 15–60).

4/ Total Sugar Content

The method used is the DUBOIS method (DUBOUS, M et al., (1956) Analytical Chemistry, 28, No. 3, pages 350–356).

In the presence of phenol and concentrated sulfuric acid, the reducing sugars give yellow-orange colored compound and the spectrophotometric reading gives a value which, from the curve DO=f(conc) obtained for standards (comprising ⅓ manose, ⅓ glucose and ⅓ galactose), permits deriving a total sugar value greater than 2 g/l and more precisely comprised between 2 and 30 g/l, particularly between 6 and 12 g/l.

The length of the glycolized chains can thus be characterized by thin layer chromatography on silica gel.

The following test solutions are arranged on the plate and migrate to give a reference:

galactose, glucose, and galacturonic acid.

Figure 1:
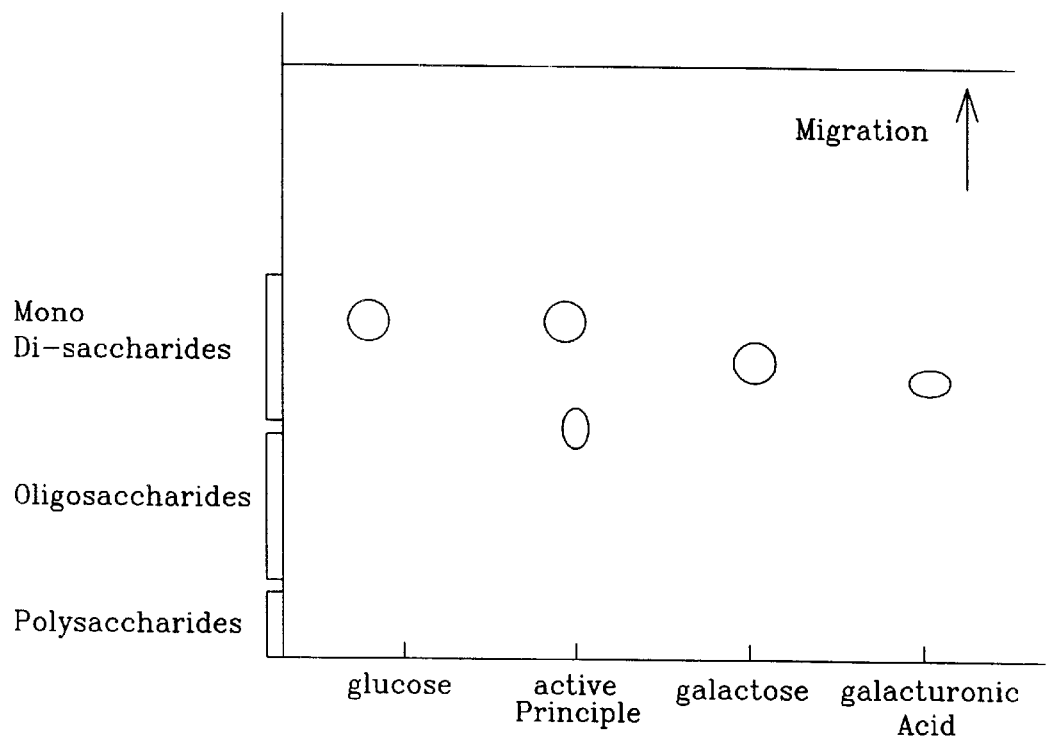
FIG. 1 shows the distribution of the different sugars.

The active principle according to the invention is also caused to migrate, and after development, there is obtained a range of FIG. 1, which shows the presence of monosaccharides and aligosaccharides in the active principle of said invention.

5/ Total Polyphenols

The content is greater than 0.2 g/l, particularly comprised between 0.2 and 5 g/l, more particularly 0.4 to 0.8 g/l, expressed as gallic acid.

The determination of the phenolic compounds is carried out by comparative reading of the results obtained with a specimen diluted relative to a standardized range of gallic acid from 0.04 to 0.12 g/l.

The intensity of coloration is thus proportional to the quantity of phenolic compounds.

III/ Effects of the Extracted Active Principle Against Cutaneous Aging

1/ Anti-Radical Activity

The operative protocol consists in measuring the protective action of the active principle of said invention on cell cultures of keratinocytes. The cellular viability is measured after chemical attack.

Figures 2, 3:
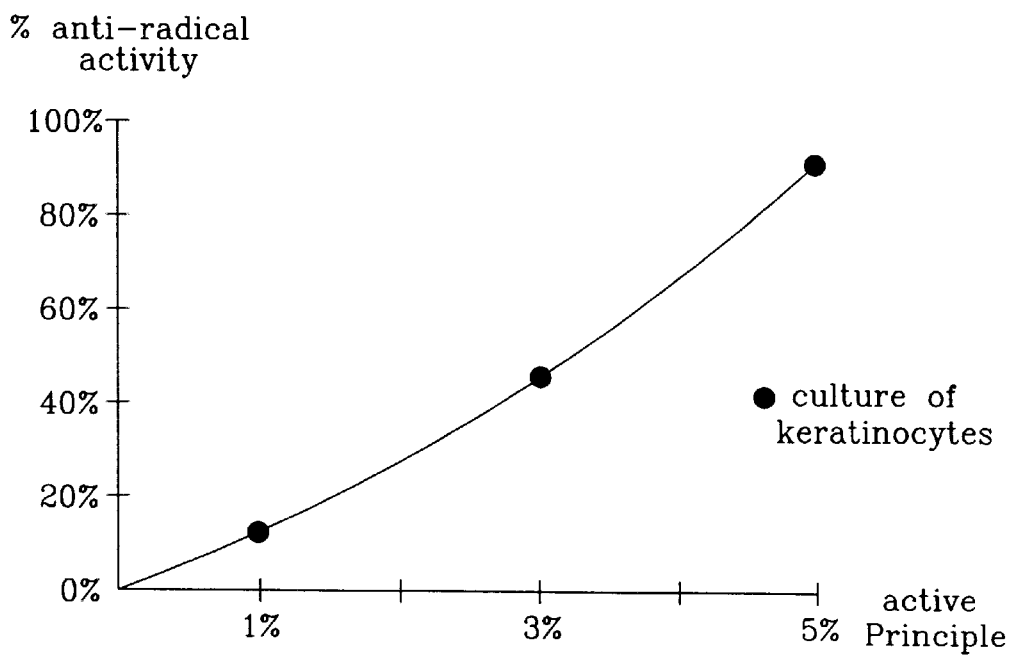
FIG. 2 shows the curve of anti-oxidant activity.
FIG. 3 shows the inhibiting effects relative to the glycolation reactions.

The results are indicated in FIG. 2, which shows the curve of the percentage of anti-radical activity as a function of the concentration of active principle according to the present invention.

The active principle according to the invention has an anti-radical activity of 90%. The protective effect is exerted on the keratinocytes.

2/ Anti-Glycolation Activity

To reproduce the glycolation reaction, a slow reaction, which is non-enzymatic, which takes place in the extracellular environment, one creates an in vitro model which relies on measurement of the formation of the derivatives of the glycolation reaction, between lysine and glucose-6-phosphate. Concurrently, a reference molecule is tested: chlorogenic acid.

The reaction mixture contains L-lysene and D-gluclose-6-phosphate in a solution buffered with sodium phosphate.

There is added to this mixture 5% of chlorogenic acid or 3, 5 and 7% of active principle extracted according to the process of the invention.

The systems are left to stand for 8 days at 37° C. shielded from light.

The results are shown in the table of FIG. 3.

It will be seen that there is good inhibition of the glycolation reaction in the presence of the active principle extracted according to the present invention.

The present invention also covers any cosmetic composition in suitable galenic form which contains in part the concentrated or dried active principle, extracted according to the process of the invention, to counter accelerated aging of the skin.

The present invention moreover covers a process for countering accelerating aging of the skin so as to counter free radicals and glycolation reactions which consists in applying preventatively to the skin such a cosmetic composition containing 0.01 to 10% of active principle and preferably 0.5% to 10%.

What is claimed is:

1. Process for the extraction of an active principle with anti-radical and anti-glycolation activity to counter cutaneous aging, characterized in that it comprises the following steps:

crushing sunflower seeds to obtain on the one hand an oil and on the other hand a de-oiled flour, aqueous solubilization of this obtained flour, in an amount of 10 to 40% by volume, hydrolysis of the proteins in the presence of a protease of acid pH, separation of the soluble and insoluble phases, inactivation of this hydrolyzed solution at a pH comprised between 2.0 and 8.0 at a temperature at least equal to 45° C., filtration to purify the active molecules, and sterilizing filtration on a membrane so as to limit the presence of microorganisms, of total mesophilic flora, of yeasts, and of molds.

2. Active principle obtained by the process of claim 1, characterized in that it comprises:

a quantity of dry material greater than 10 g/l, a pH comprised between 3.0 and 10.0, a quantity of proteins comprised between 5 and 30 g/l, a quantity of total sugar greater than 2 g/l, a quantity of total polyphenols greater than 0.2 g/l, expressed as gallic acid.

3. Cosmetic composition to counter glycolation reactions, characterized in that it comprises at least a portion of the active principle according to claim 2, concentrated or dried, associated in any suitable galenic form.

4. Cosmetic composition to counter formed free radicals, characterized in that it comprises at least a portion of active principle according to claim 2, concentrated or dried, associated in any suitable galenic form.

5. Process for countering accelerated aging of the skin so as to counter free radicals and glycolation reactions, characterized in that there is applied preventatively to the skin a cosmetic composition containing an active principle according to claim 2 in an amount with 0.01 to 50% active principle.

6. Process for countering accelerated aging of the skin so as to counter free radicals and glycolation reactions, characterized in that there is applied preventatively to the skin a cosmetic composition according to claim 5 containing 0.5 to 10% of active principle.

7. The active principle of claim 2, wherein the quantity of dry material is between 10 and 100 g/l.

8. The active principle of claim 2, wherein the quantity of dry material is between 25 and 38 g/l.

9. The active principle of claim 2, wherein the pH is between 5.0 and 6.0.

10. The active principle of claim 2, wherein the quantity of proteins is between 6 and 10 g/l.

11. The active principle of claim 2, wherein the quantity of total sugar is between 2 and 30 g/l.

12. The active principle of claim 2, wherein the quantity of total sugar is between 6 and 12 g/l.

13. The active principle of claim 2, wherein the quantity of total polyphenols is between 0.2 and 5 g/l.

14. The active principle of claim 2, wherein the quantity of total polyphenols is between 0.4 and 0.8 g/l.

15. The active principle of claim 8, wherein the pH is between 5.0 and 6.0.

16. The active principle of claim 15, wherein the quantity of proteins is between 6 and 10 g/l.

17. The active principle of claim 16, wherein the quantity of total sugar is between 6 and 12 g/l.

18. The active principle of claim 17, wherein the quantity of total polyphenols is between 0.4 and 0.8 g/l.

* * * * *